(12) United States Patent
Agara Venkatesha Rao et al.

(10) Patent No.: US 11,324,428 B2
(45) Date of Patent: May 10, 2022

(54) MULTI-SPHERE HEAD MODEL FOR DIPOLE LOCALIZATION WITHOUT GHOST SPHERES

(71) Applicants: Krishna Prasad Agara Venkatesha Rao, Bengaluru (IN); Srinidhi Srinivasa, Bengaluru (IN)

(72) Inventors: Krishna Prasad Agara Venkatesha Rao, Bengaluru (IN); Srinidhi Srinivasa, Bengaluru (IN)

(73) Assignee: Ricoh Company, Ltd., Tokyo (JP)

( * ) Notice: Subject to any disclaimer, the term of this patent is extended or adjusted under 35 U.S.C. 154(b) by 546 days.

(21) Appl. No.: 16/353,549

(22) Filed: Mar. 14, 2019

(65) Prior Publication Data
US 2020/0289007 A1 Sep. 17, 2020

(51) Int. Cl.
*A61B 5/246* (2021.01)
*A61B 5/00* (2006.01)
*A61B 34/10* (2016.01)
*G06K 9/00* (2022.01)

(52) U.S. Cl.
CPC ............ *A61B 5/246* (2021.01); *A61B 5/4064* (2013.01); *A61B 5/6814* (2013.01); *A61B 34/10* (2016.02); *A61B 2034/107* (2016.02); *G06K 9/0057* (2013.01)

(58) Field of Classification Search
CPC ....... A61B 5/246; A61B 5/245; A61B 5/4064; A61B 5/6814; A61B 34/10; A61B 2034/107; G06K 9/0057
See application file for complete search history.

(56) References Cited

U.S. PATENT DOCUMENTS

2005/0020933 A1* 1/2005 Sato .............. A61B 5/245
600/544

FOREIGN PATENT DOCUMENTS

| JP | 07227385 A | * | 8/1995 |
| JP | H07-227385 A | | 8/1995 |
| JP | 10276996 A | * | 10/1998 |
| JP | H10-276996 A | | 10/1998 |

OTHER PUBLICATIONS

Huang, M. X., John C. Mosher, and R. M. Leahy. "A sensor-weighted overlapping-sphere head model and exhaustive head model comparison for MEG." Physics in Medicine & Biology 44.2 (1999): 423. (Year: 1999).*
Japan Patent Office, Office Action, JP Patent Application No. 2020-041438, dated Feb. 24, 2021, six pages.
Lalancette, M. et al., "Evaluation of multiple-sphere head models for MEG source localization," Physics in Medicine & Biology 56, Aug. 9, 2011, pp. 5621-5635.
United States Office Action, U.S. Appl. No. 16/353,536, filed Jul. 30, 2021, 17 pages.

* cited by examiner

*Primary Examiner* — Sean D Mattson
(74) *Attorney, Agent, or Firm* — Fenwick & West LLP

(57) ABSTRACT

In one aspect, a computer-implemented method corrects a multi-sphere head model used in dipole localization for a set of magnetic field sensors (MEG sensors) by replacing ghost spheres with replacement spheres that are not ghost spheres. One type of ghost sphere completely encloses the brain volume but is so large that a center of the sphere is outside the brain volume. Another type of ghost sphere lies entirely outside the brain volume. Various approaches for correcting ghost spheres are disclosed.

15 Claims, 12 Drawing Sheets

MULTI-SPHERE HEAD MODEL FOR DIPOLE LOCALIZATION WITHOUT GHOST SPHERES

BACKGROUND

1. Technical Field

This disclosure relates generally to generating multi-sphere head models, as may be used in dipole localization for magnetoencephalography (MEG).

2. Description of Related Art

In magnetoencephalography (MEG), the brain's electrical activity causes a magnetic field and this is captured by magnetic field sensors (MEG sensors) positioned at different locations around the brain. These signals can be analyzed for various purposes, such as diagnosing medical conditions, measuring brain function, and conducting research. They are especially well-suited for detecting temporal responses. In one common scenario, the subject undergoes different types of stimuli or performs different types of activity and the resulting MEG signals are reviewed for certain responses or characteristics. For example, if a known stimulus is presented to the subject, the MEG signals may be observed for a response of a certain frequency at a certain time delay after the stimulus. The presence or absence of that response may be an indication of a medical condition. Statistical analysis can also be performed across populations of subjects, for example between groups with and without a medical condition.

In many MEG applications, it is useful to have a multi-sphere model (aka overlapping sphere model) of a person's head. A multi-sphere model includes one sphere for each MEG sensor. The sphere is selected to match a local curvature of the brain surface in the area most relevant to the MEG sensor. These can then be used in the dipole localization step, which is a common step for many MEG processing pipelines. However, in many cases, the multi-sphere model generated using conventional approaches results in ghost spheres. In a ghost sphere, a significant percentage of the sphere's volume lies outside the brain. The use of ghost spheres results in models in which a large number of dipoles are located outside the brain, which does not match the physical reality.

Thus, there is a need for better approaches to generate overlapping sphere models, including for MEG and other encephalography applications.

SUMMARY

In one aspect, the present disclosure provides a computer-implemented method for correcting a multi-sphere head model used in dipole localization for a set of magnetic field sensors (MEG sensors) by replacing ghost spheres with replacement spheres that are not ghost spheres. One type of ghost sphere completely encloses the brain volume but is so large that a center of the sphere is outside the brain volume. Another type of ghost sphere lies entirely outside the brain volume. Various approaches for correcting ghost spheres are described below.

Other aspects include components, devices, systems, improvements, methods, processes, applications, computer readable mediums, and other technologies related to any of the above. The following examples use spheres as a basic shape, but other shapes may also be used, for example ellipsoids.

BRIEF DESCRIPTION OF THE DRAWINGS

Embodiments of the disclosure have other advantages and features which will be more apparent from the following detailed description and the appended claims, when taken in conjunction with the examples in the accompanying drawings, in which:

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Figures 1, 4:
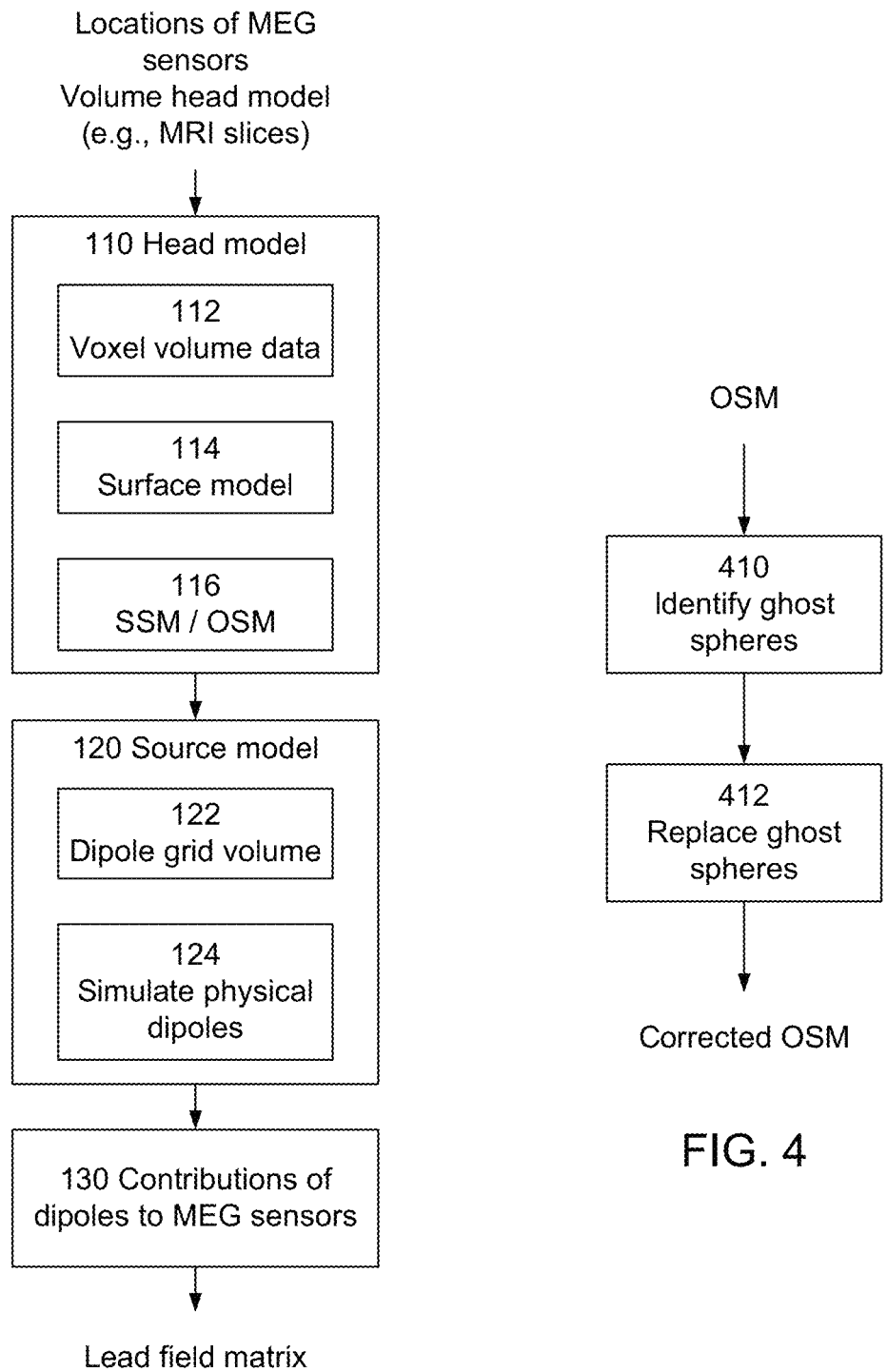
FIG. 1 (prior art) is a flow diagram of a magnetoencephalography (MEG) forward model.
FIG. 4 is a flow diagram for correcting ghost spheres in a multi-sphere head model.

FIG. 1 (prior art) is a flow diagram of a magnetoencephalography (MEG) forward model. In MEG, magnetic field sensors are positioned at different locations around the brain. For example, the patient may position his head inside equipment with an array of MEG sensors or the patient may wear headgear containing an array of MEG sensors. The brain's electrical activity produces a magnetic field and the magnetic field at different locations is measured by the MEG sensors. The process in FIG. 1 is a forward model, which estimates the magnetic field at each MEG sensor for a given pattern of brain activity. This forward model can then be used to solve the inverse problem: Given measurements of the magnetic field at each MEG sensor, estimate the electrical brain activity that produced the measured magnetic fields.

The process has three main steps. A model of the patient's head is generated 110. A model of the sources of magnetic field in the brain is generated 120. The source model 120 is applied to the head model 110 to estimate 130 the magnetic field at each of the MEG sensors.

In this example, assume that MM slices of the patient's head are available. The head model 110 may be generated as follows. The MRI slices are first assembled into a three-dimensional volume model of the patient's head, for example a three-dimensional model that represents the patient's head as voxels 112. A surface model 114 of the relevant structure is generated from the three-dimensional volume model. The surface model 114 is used to generate 116 the head model, for example a single sphere head model (SSM) or an overlapping sphere head model (OSM). In the following examples, the head model is based on spheres but other shapes may also be used, for example ellipsoids.

Figure 2A:
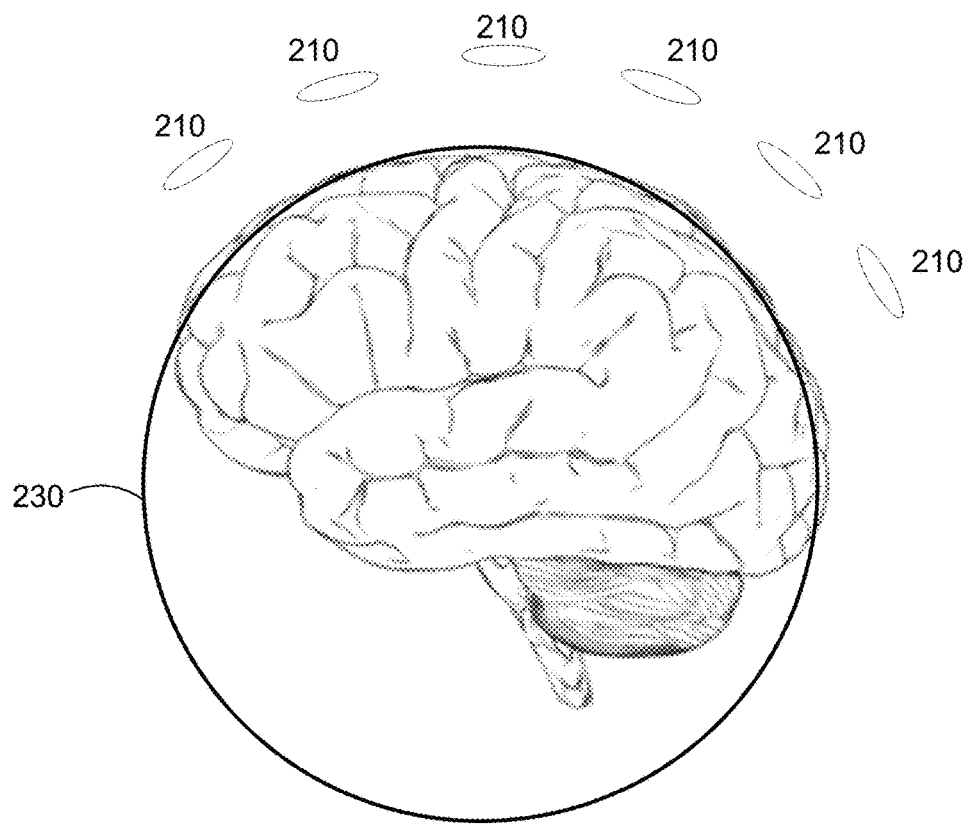
FIG. 2A shows a single sphere head model.
Figure 2B:
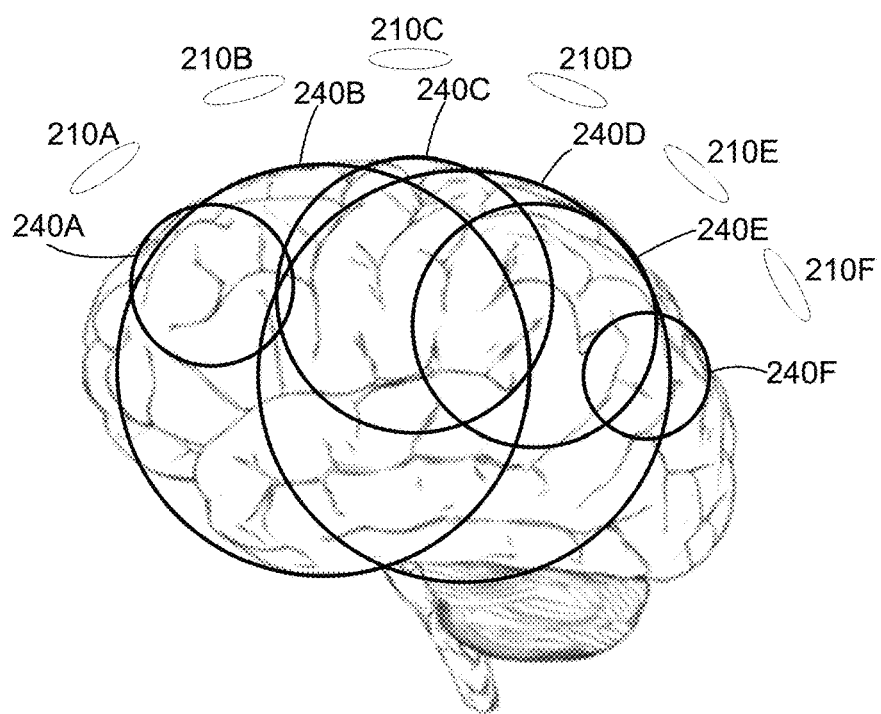
FIG. 2B shows an overlapping sphere (multi-sphere) head model.

FIGS. 2A and 2B illustrate the single sphere head model and the overlapping sphere head model (also known as a multi-sphere model). In both figures, MEG sensors 210 are positioned around the brain 220. In the SSM (FIG. 2A), the patient's brain is represented by a single sphere 230 based on fit to the surface model. In the OSM (FIG. 2B), the patient's brain is represented by multiple overlapping spheres 240A-F, one for each corresponding MEG sensor 210A-F. Sphere 240A corresponds to MEG sensor 210A, sphere 240B to MEG sensor 210B, etc. The spheres 240 are chosen in part to match the local curvature of the brain's surface in the vicinity of the corresponding MEG sensor 210. For convenience, the one sphere 230 in the SSM may be referred to as a global sphere because the same sphere is used for all MEG sensors 210, and each of the spheres 240A-F in the OSM may be referred to as local spheres. Returning to FIG. 1, the SSM/OSM 116 is used to model the propagation of magnetic fields from sources within the brain to the MEG sensors.

The sources within the brain are typically modelled 120 as dipole sources. The synaptic electrical activity in the brain may be modelled as current dipoles. The model includes a distribution 122 of dipoles throughout the volume of the brain. Given a dipole at a certain location of the brain and given the model of the brain volume (e.g., OSM or SSM), the magnetic field created by each dipole is simulated 124. The contributions of all dipoles are aggregated 130 to estimate the total magnetic field at each MEG sensor. This is referred to as the lead field matrix.

Conventional approaches to generating the OSM (step 116 above) may result in local spheres that are "ghost spheres." In conventional approaches, each local sphere 240 is generated based on the curvature of the brain's surface in the local vicinity of the corresponding MEG sensor 210. However, if there is a sparsity of sample points for the brain's surface or if the points are excessively noisy or if the brain's surface has an unusual local curvature, the resulting sphere may not work well with later steps of MEG processing.

Figure 3A:
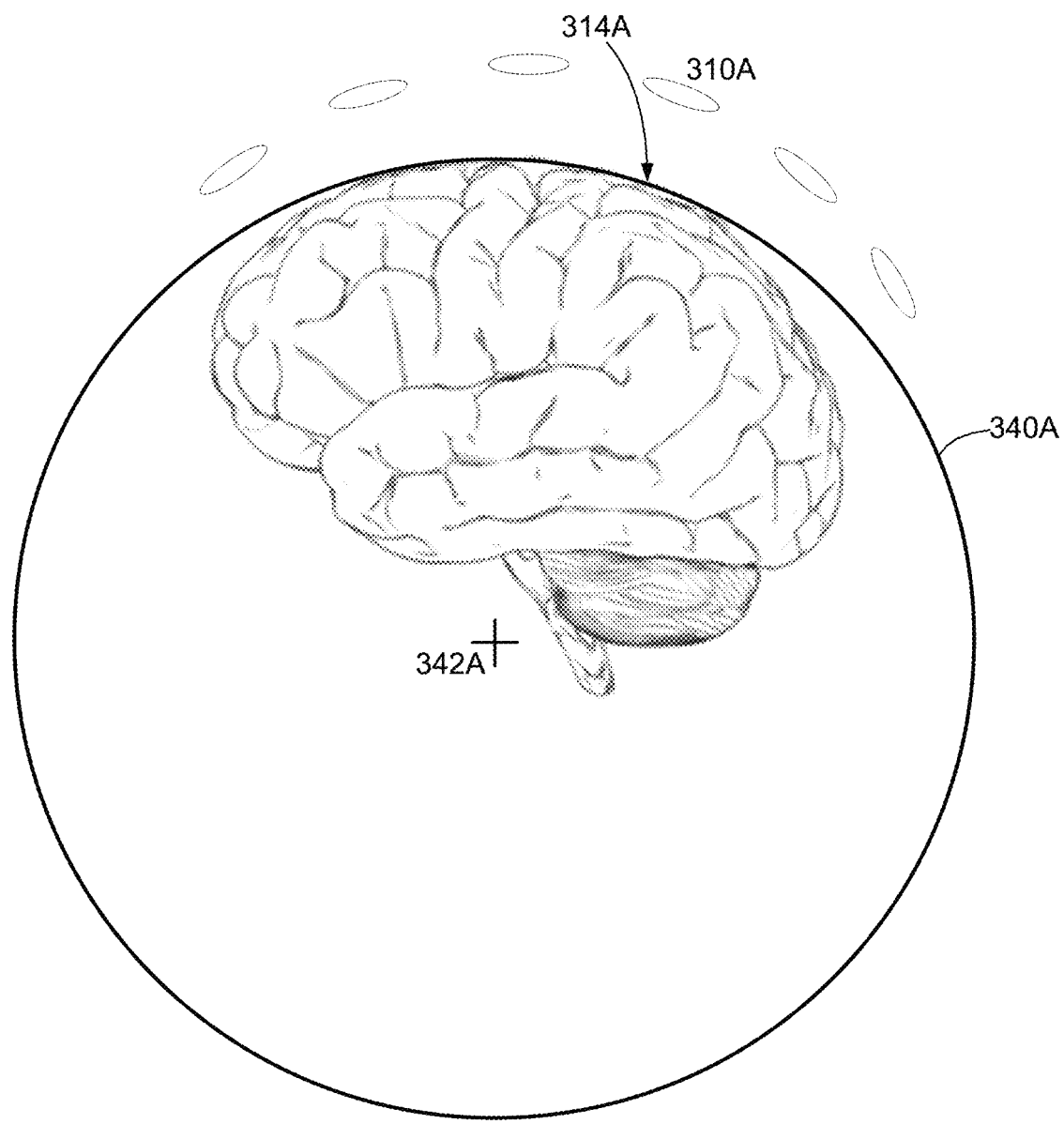
FIGS. 3A and 3B show two types of ghost spheres.
Figure 3B:
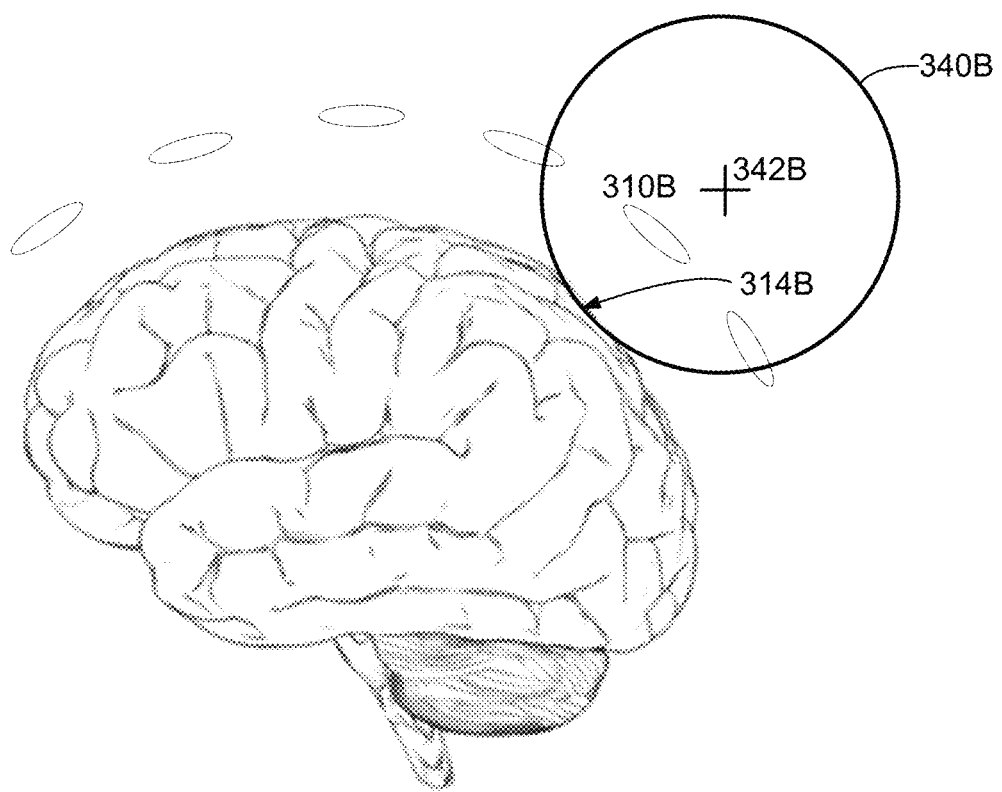

FIGS. 3A and 3B show examples of two types of ghost spheres. In each figure, a local surface patch 314 of the brain closest to the MEG sensor 310 can be used to define outward and inward directions relative to the brain. The outward direction is the direction from the local surface patch 314 towards the MEG sensor 310, and the inward direction is the direction from the local surface patch 314 away from the MEG sensor 310.

In FIG. 3A, the sphere 340A with center 342A was generated for MEG sensor 310A. However, the surface model of the brain results in a sphere 340A that is large compared to the brain. In this example, the center 342A of the sphere is inwards of the local surface patch 314A. That is, the center 342A of the sphere and the MEG sensor 310A are located on opposite sides of the local surface patch 314A. Usually, this is desirable because the volume of the brain is located on the inward side of the local surface patch. However, the sphere has such a large diameter that the center 342A of the sphere falls outside the brain volume. This may be problematic because fifty percent or more of the sphere's volume may lie outside the brain volume. If subsequent modeling places dipoles in this non-overlapping region, this is a large number of dipoles that physically do not exist.

In FIG. 3B, the sphere 340B has a center 342B that is outwards of the local surface patch 314B. That is, the center 342B of the sphere and the MEG sensor 310B are both located on the outward side of the local surface patch 314B. This may occur, for example, if the sample points for the surface patch 314B suggest that it is locally concave. In this example, the sphere 340B typically is not overlapping with the brain volume. As in FIG. 3A, this may also be problematic because dipoles located in the sphere 340B will lie outside the brain volume.

FIG. 4 is a flow diagram for correcting a multi-sphere head model. Spheres in the OSM that are ghost spheres are identified 410. This may be accomplished using the characteristics of ghost spheres described above. If a sphere's center lies outside the brain volume or if a significant fraction of a sphere falls outside the brain volume, it may be identified as a ghost sphere. The ghost spheres are not suitable for modeling dipole localization in the brain volume, typically because a significant fraction of the ghost sphere falls outside the brain volume. As a result, the ghost spheres are replaced 412 by other spheres that are not ghost spheres, resulting in a corrected OSM.

Various approaches to generate replacement spheres are described below. In one correction approach, ghost spheres are replaced by the global sphere generated for the single sphere model. This results in a hybrid approach. Some of the MEG sensors will use the local sphere generated for that sensor, and the rest of the MEG sensors will use the global sphere. In a variation, the global sphere may be generated based on only those MEG sensors that have ghost spheres, rather than based on all MEG sensors as is the case in a true SSM approach.

In another approach, the replacement sphere is selected from a family of candidate replacement spheres. For example, the family of candidate replacement spheres may all have centers that lie along a common line: the line defined by the MEG sensor and the point on the brain surface closest to the MEG sensor, or the line defined by the MEG sensor and the center of the global sphere described previously, or the line defined by the MEG sensor and the center of the brain volume. The family of candidate replacement spheres may also be constrained in diameter. For example, they may all have diameters that do not exceed a smallest diameter that completely encloses the brain volume. As another example, the family of candidate replacement spheres may all pass through the point on the brain surface closest to the MEG sensor. In one approach the replacement sphere is selected from the family of candidate replacement spheres based on a fit between the replacement sphere and the brain surface.

Figure 5:
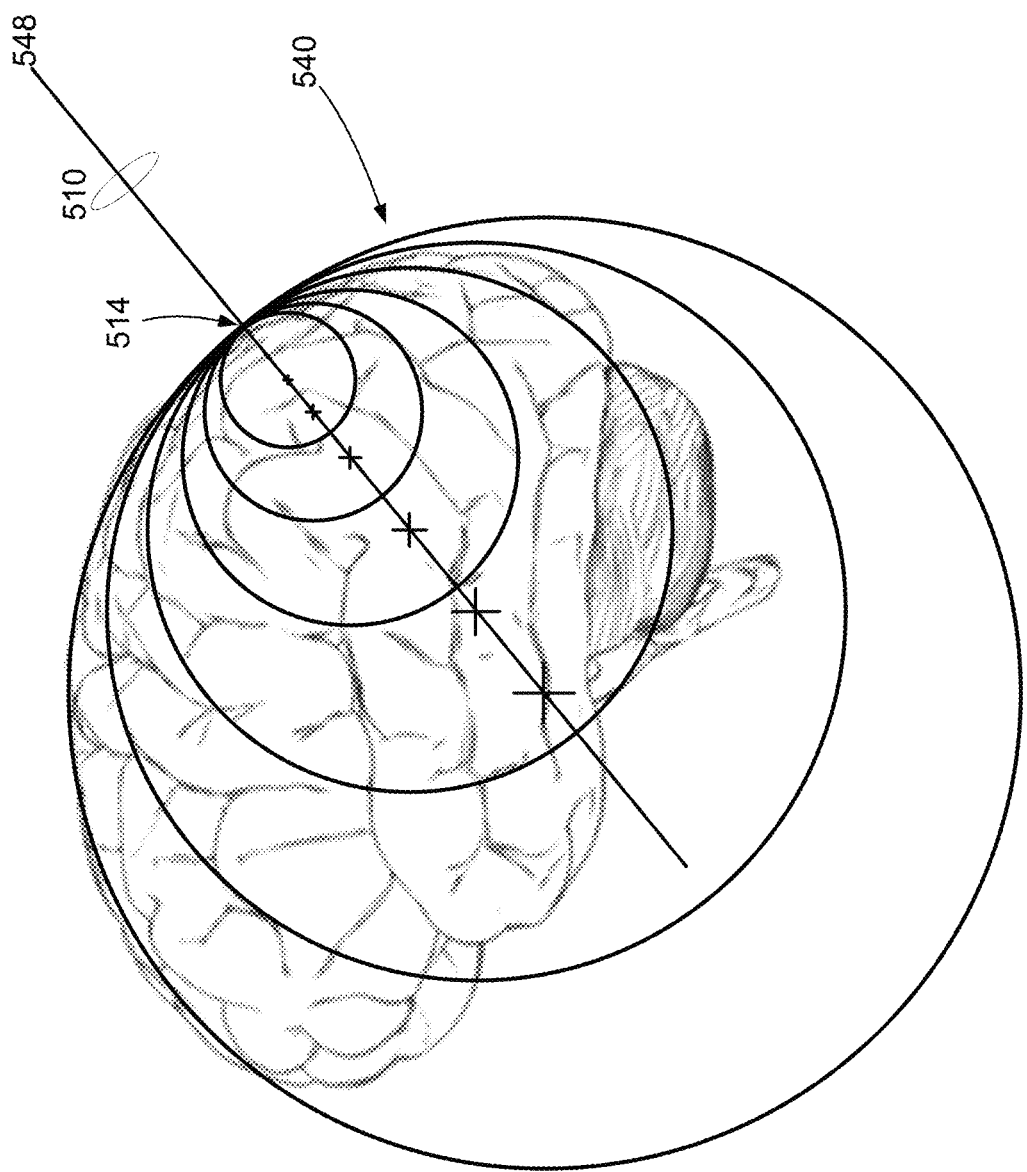
FIG. 5 shows a family of candidate replacement spheres.

FIGS. 5-9 show some examples. FIG. 5 shows a family of candidate replacement spheres 540 defined as follows. A line 548 is defined by the MEG sensor 510 and the point 514 on the brain surface that is closest to the MEG sensor. The centers of the replacement spheres 540 lie on line 548 on the inward side of point 514. In addition, the replacement spheres 540 are contrained to include this surface point 514. Increasing the diameter of the sphere yields the family of candidate replacement spheres 540. In this example, the maximum diameter is also constrained by the smallest sphere that encloses the brain volume.

One of the candidate spheres is selected as the replacement sphere, typically based on a fit between the replacement sphere and the brain surface. The selection can be solved as an optimization problem. The family of candidate spheres can be parameterized as a function of the sphere diameter in a range of [0, max diameter]. The problem is then to select the sphere diameter that optimizes a cost function. Examples of cost functions are based on local curvature fitting based on the L1 error, the L2 error, or using eigen-solvers (both analytical and approximation classes of sphere fitting fitting the curvature of a local surface patch).

Figure 6A:
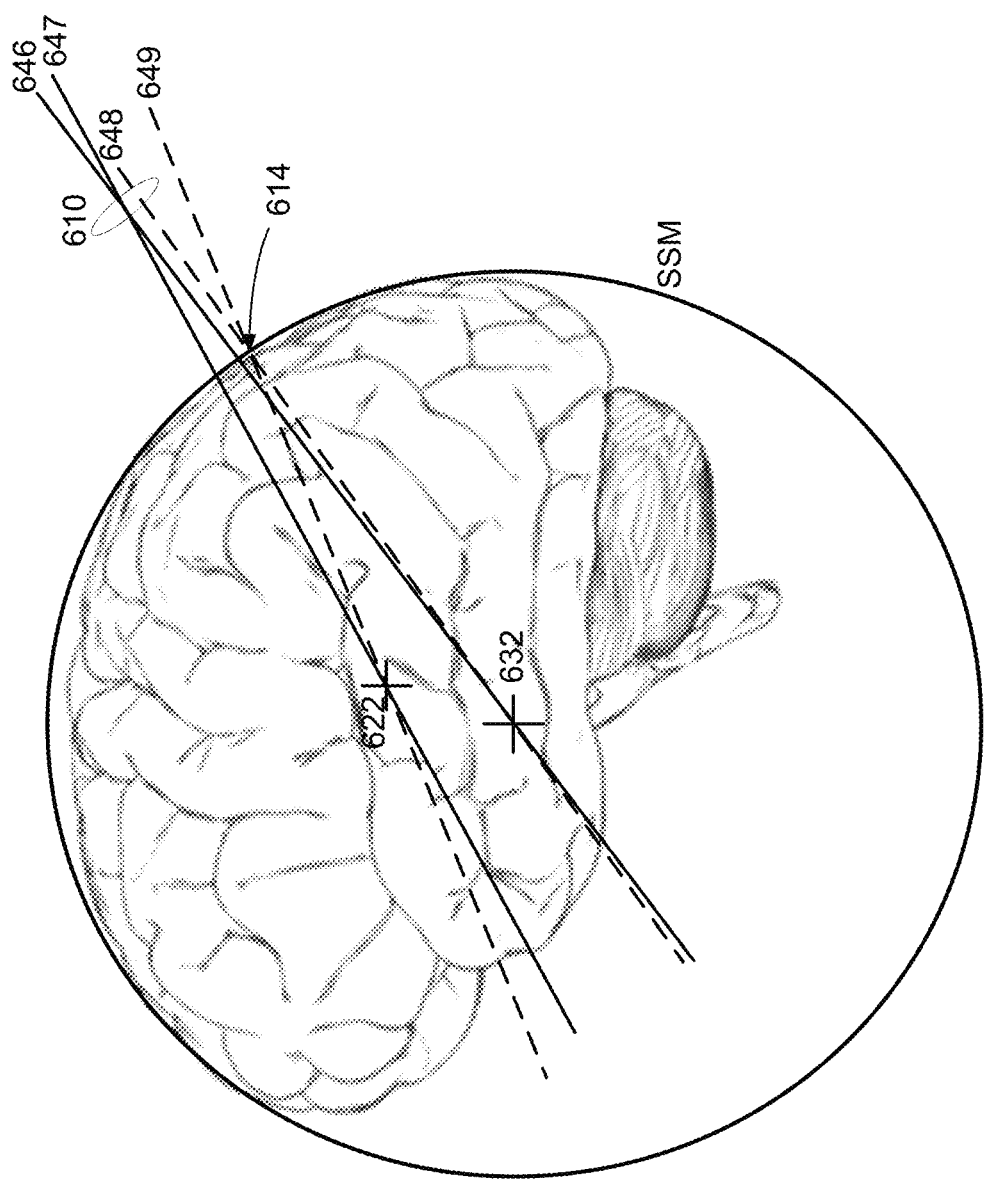
FIG. 6A shows different lines that may be used to define families of candidate replacement spheres.

In FIG. 5, the centers of the candidate replacement spheres were constrained to lie along line 548. Other lines could be selected, as shown in FIG. 6A. FIG. 6A shows the following points: location 610 of the MEG sensor, the closest surface point 614 to the MEG sensor, the center 632 of the global sphere (from the SSM of FIG. 2A), and the center 622 of the brain volume. Different pairs of points define other lines: line 646 through the MEG sensor 610 and the SSM center 632, line 647 through the MEG sensor 610 and the brain center 622, line 648 through surface point 614 and the SSM center 632, and line 649 through surface point 614 and the brain center 622, for example. The lines through surface point 614 are dashed in order to more easily distinguish the lines from each other. Other families of candidate replacement spheres may be defined by requiring the center of the replacement sphere to lie on any of these lines. Other lines may also be used, for example lines that are normal to the surface of the brain.

Figure 6B:
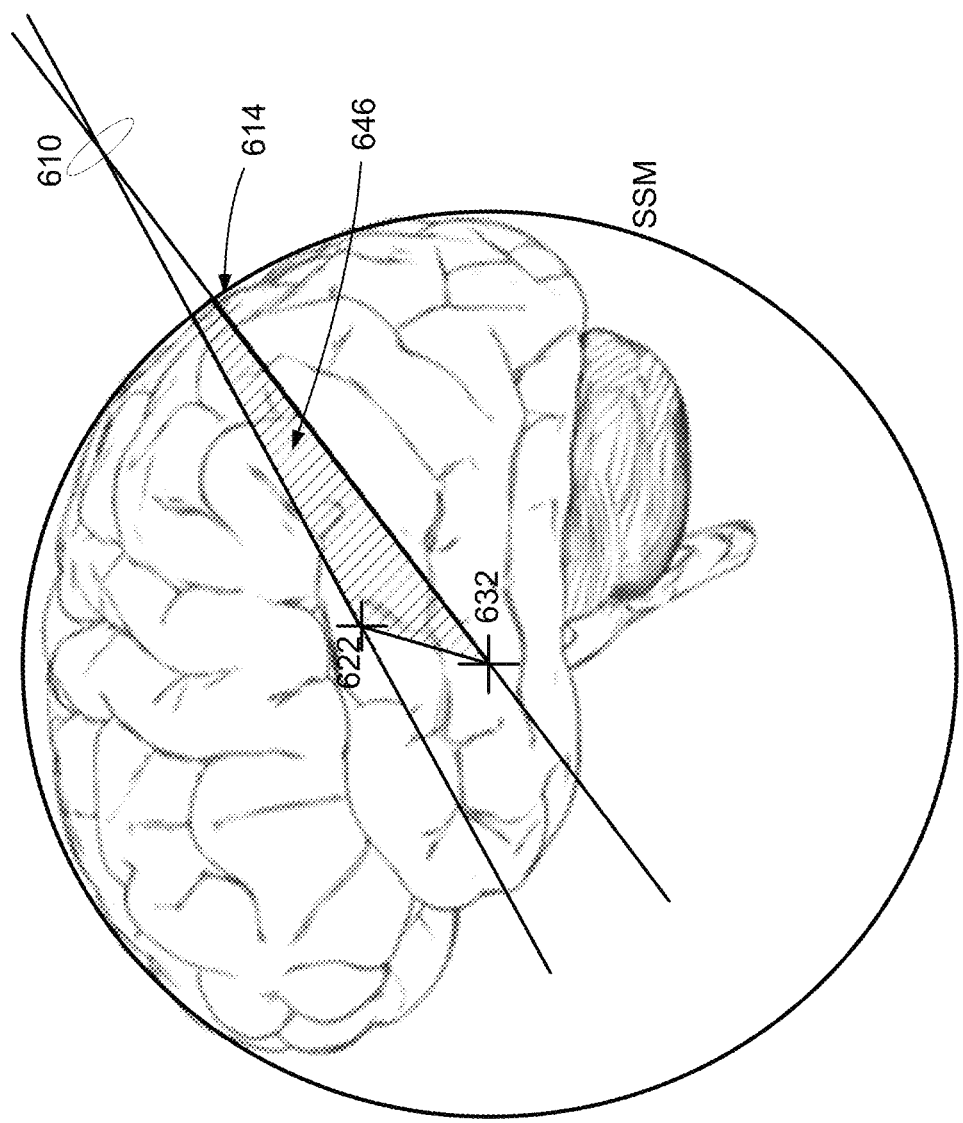
FIG. 6B shows an area that may be used to define a family of candidate replacement spheres.
Figure 7A:
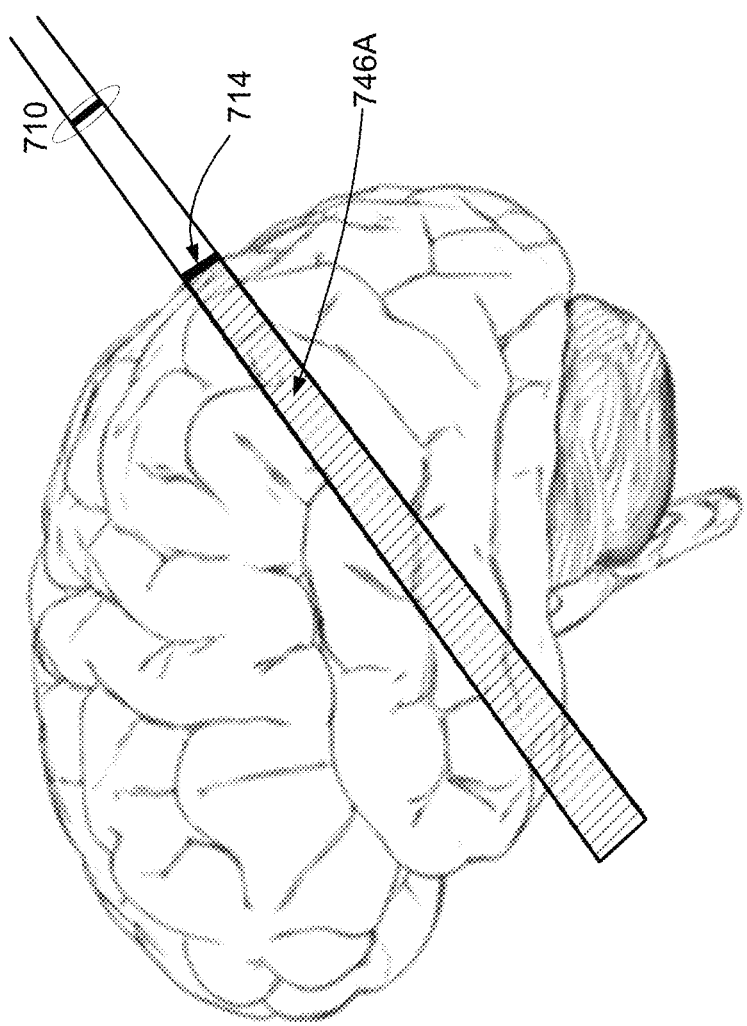
FIGS. 7A and 7B show volumes that may be used to define a family of candidate replacement spheres.
Figure 7B:
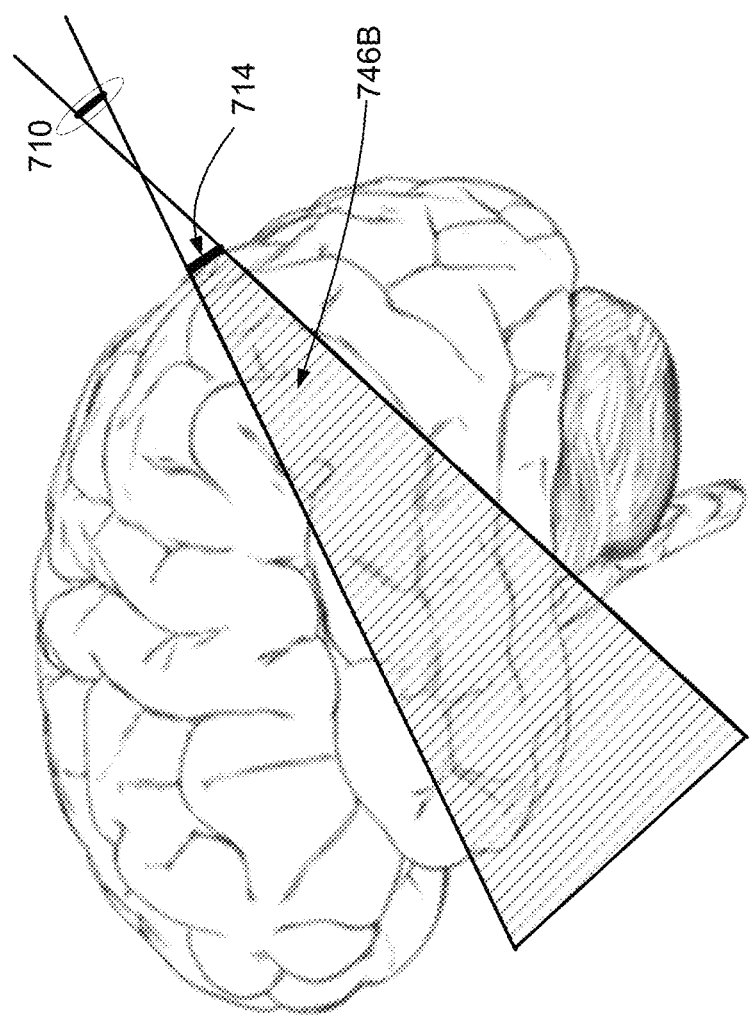

The locus of possible locations for the sphere's center may also be an area or volume, rather than a line. For example, as shown in FIG. 6B, it may be the triangle with vertices 610-632-622, but considering only those points that are on the inward side of point 614. The resulting locus of possible center points is the trapezoid 646. FIG. 7 shows another example where the location of the MEG sensor is defined by an area 710 rather than a point, and the closest surface patch is also defined by an area 714 rather than a point. The locus of possible center points is defined by a projection of area 710 through area 714, which defines a three-dimensional volume 746. FIG. 7A shows a more restrictive projection 746A and FIG. 7B shows a more expansive projection 746B. Volumes may also be defined by starting with a line or area and defining a volume that is within a certain distance of the line or area.

The region of interest, whether it is a line, area or volume, is typically defined by at least two of the following: (a) the location of the MEG sensor (whether defined as a point, area or volume), (b) the region of brain surface closest to the MEG sensor (which is typically a point or surface area), and (c) the location of the brain volume (e.g., the center of the SSM global sphere, or the centroid or center of mass of the brain volume).

Figure 8:
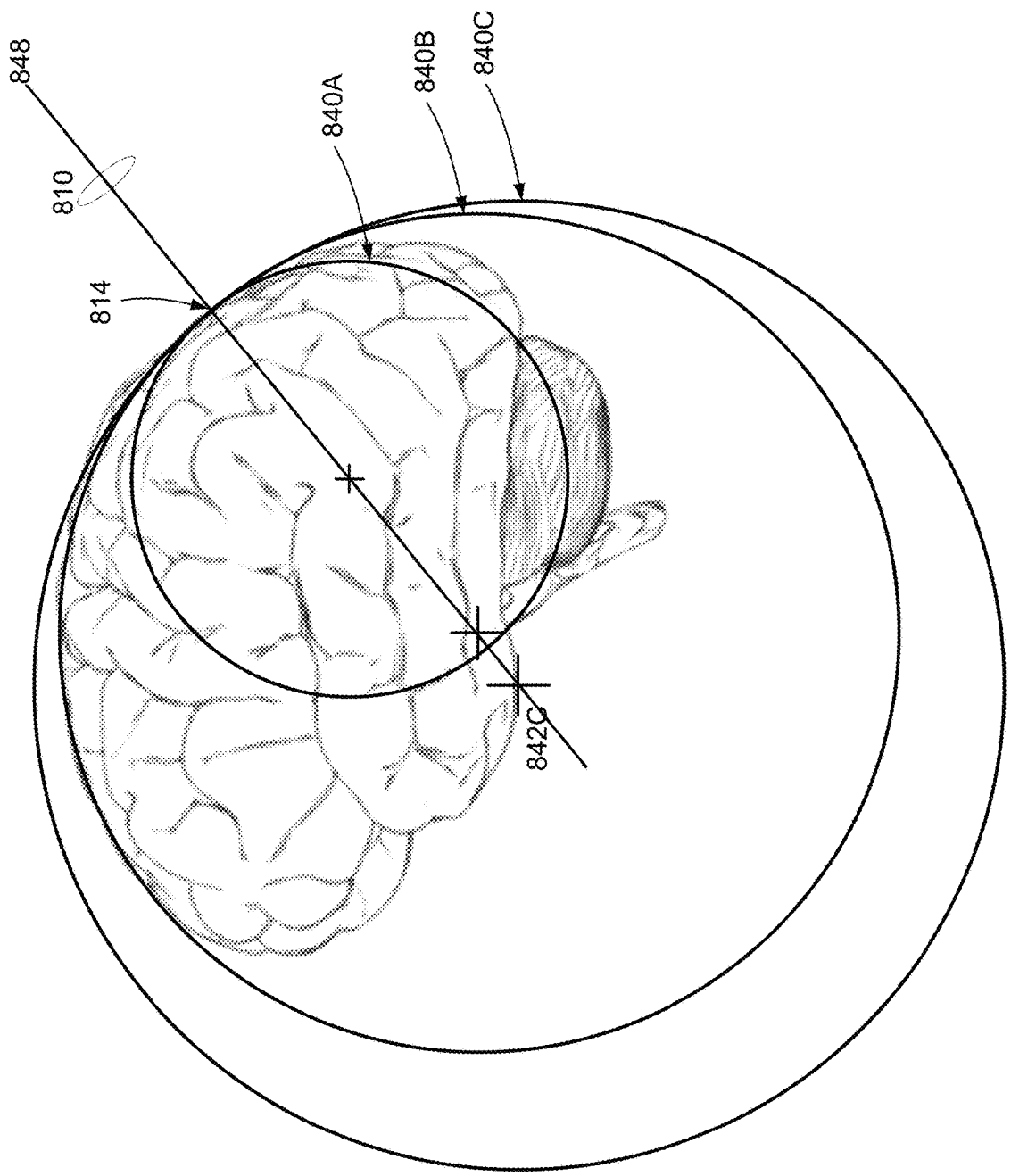
FIG. 8 shows different spheres that may be used to define a maximum diameter for a family of candidate replacement spheres.

The family of candidate replacement spheres may also be constrained to be smaller than a maximum size. The maximum diameter of the replacement sphere may be selected so that the replacement sphere is not a ghost sphere. FIG. 8 shows the same situation as FIG. 5 but also shows spheres of different maximum diameters, assuming that the center of the sphere lies along line 848 and the sphere includes surface point 814. For sphere 840A, the maximum diameter is defined by the largest sphere that is enclosed by the brain volume. For sphere 840B, it is defined by the smallest sphere that encloses the brain volume (same as in FIG. 5). For sphere 840C, it is defined by requiring that the center 842C of the sphere remains inside the brain volume.

Figure 9:
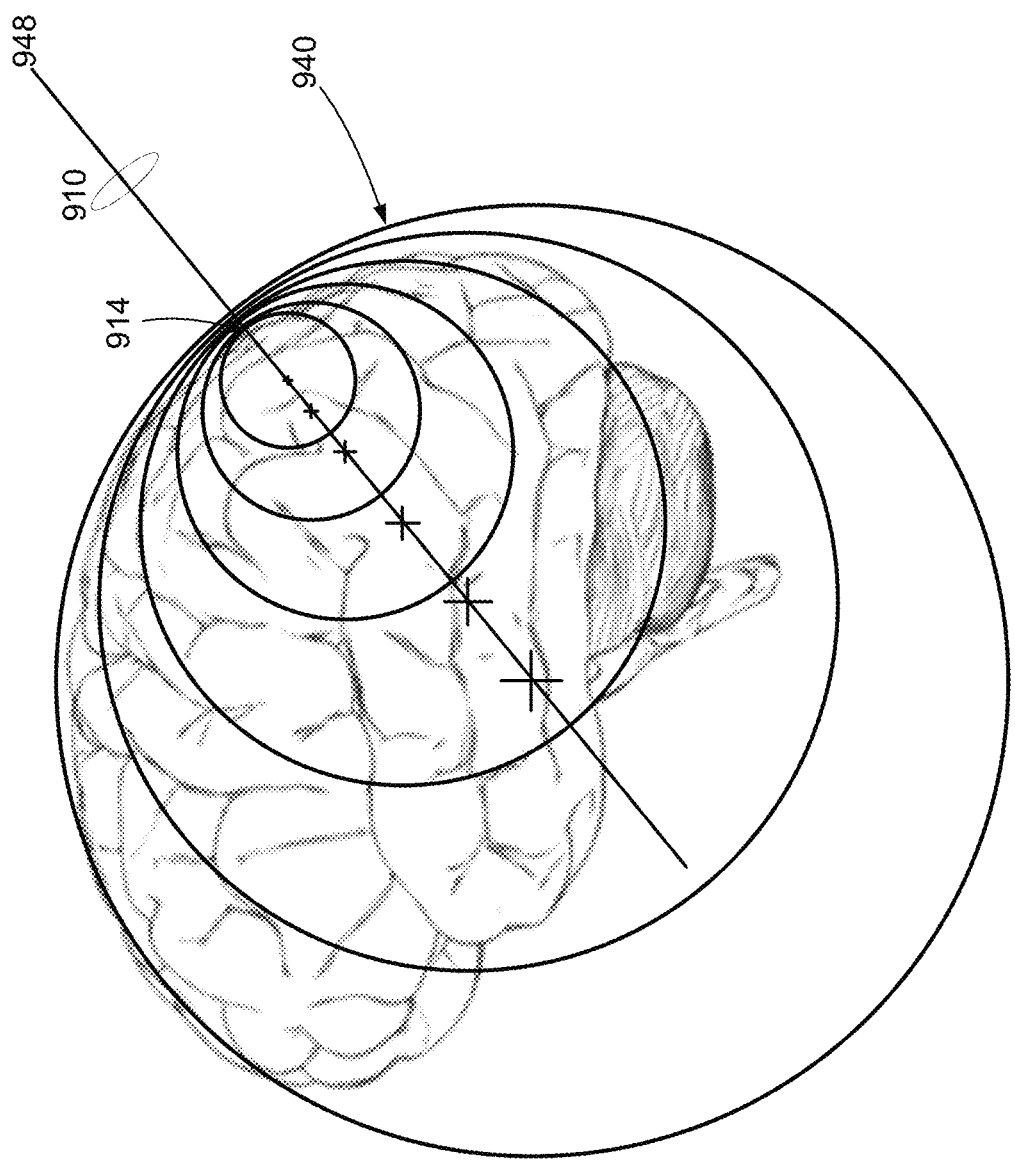
FIG. 9 shows another family of candidate replacement spheres.

In FIG. 5, the family of candidate replacement spheres is also constrained to include point 514, which is the point closest to the MEG sensor. That is, every candidate replacement sphere 540 passes through point 514. Other variations of this constraint are also possible. In FIG. 9, the candidate replacement spheres 940 are constrained to have centers that lie on line 948, defined by the location 910 of the MEG sensor and the closest surface point 914. However, the spheres are not required to all pass through the surface point 914. Rather, each sphere 940 is located so that it makes a best fit to a local patch of the brain's surface. Thus, spheres 940 may be shifted slightly off of point 914.

Figure 10:
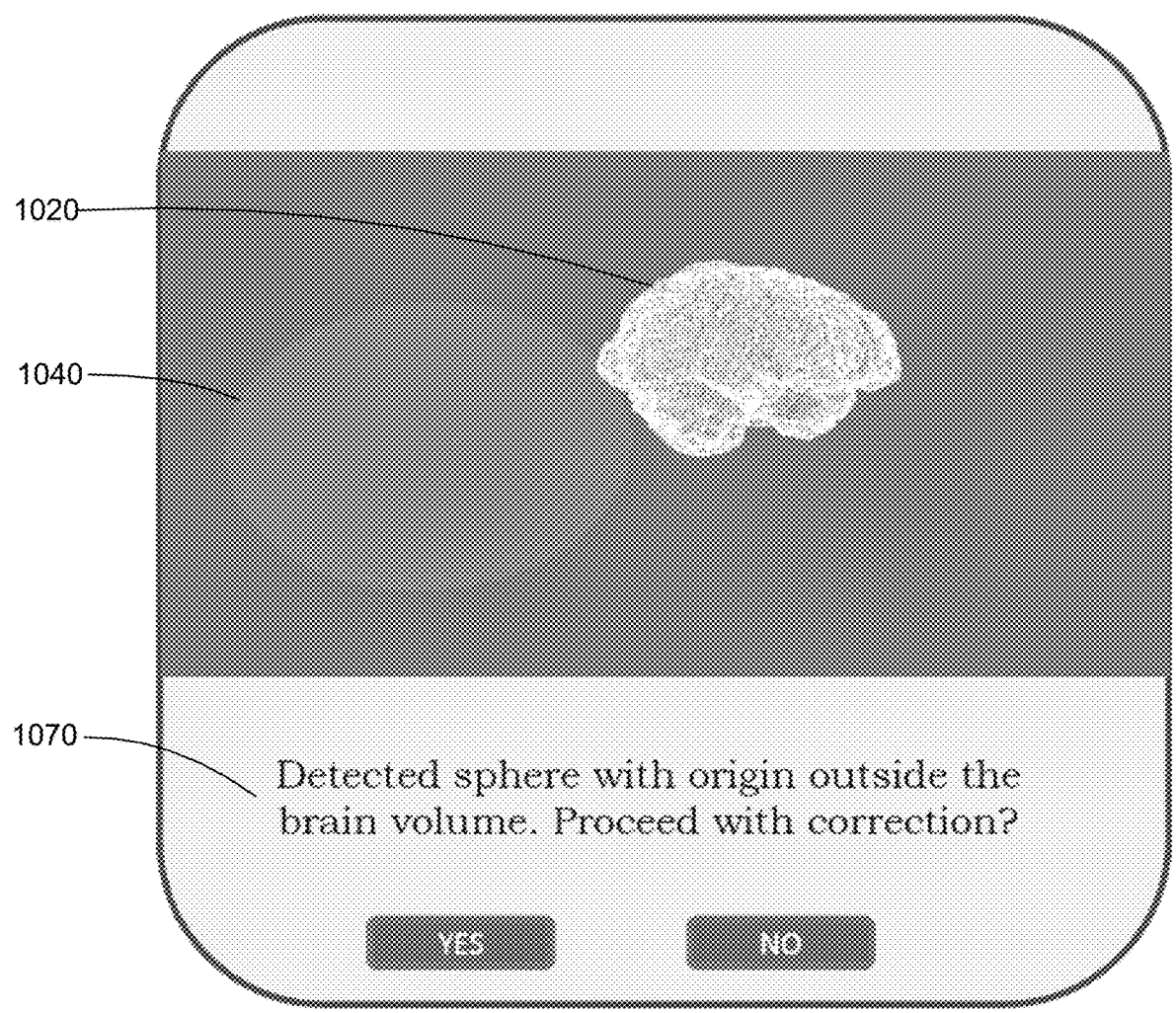
FIG. 10 shows a user interface for controlling the correction of ghost spheres.

In some implementations, a user interface allows the user to control the correction process. In FIG. 10, the user interface shows a ghost sphere 1040 that lies outside the brain 1020. The user is prompted 1070 whether correction should be attempted. The user responds by giving a user instruction whether to compute a replacement sphere for that particular ghost sphere. The next screen of the user interface could then show the computed replacement sphere and prompt the user whether to replace the ghost sphere with the calculated replacement sphere. The user interface displays the various spheres in relation to the brain so that the user can visualize the situation.

In yet another approach, rather than correcting ghost spheres, a multi-sphere head model is generated subject to constraints that prevent the generation of ghost spheres in the first place. For example, the centers of the spheres may be constrained to lie inside the brain volume. The diameters of the spheres may be constrained so that they do not exceed some maximum, for example the diameter of the smallest sphere that completely encloses the brain volume. The constraints described above for defining families of candidate replacement spheres may also be used as constraints to prevent the generation of ghost spheres in the first place.

As a final example, ghost spheres may result from fitting too few data points. To avoid this, the spheres may be fit to a set of points on the brain surface, but subject to the constraint that at least a predefined number of points are used to fit the sphere.

Although the detailed description contains many specifics, these should not be construed as limiting the scope of the invention but merely as illustrating different examples. It should be appreciated that the scope of the disclosure includes other embodiments not discussed in detail above. For example, ellipsoids or other shapes may be used instead of spheres. In that case, a multi-ellipsoid head model is developed in place of a multi-sphere head model and the concept of ghost spheres is replaced by ghost ellipsoids. Various other modifications, changes and variations which will be apparent to those skilled in the art may be made in the arrangement, operation and details of the method and apparatus disclosed herein without departing from the spirit and scope as defined in the appended claims. Therefore, the scope of the invention should be determined by the appended claims and their legal equivalents.

Alternate embodiments are implemented in computer hardware, firmware, software, and/or combinations thereof. Implementations can be implemented in a computer program product tangibly embodied in a computer-readable storage device for execution by a programmable processor; and method steps can be performed by a programmable processor executing a program of instructions to perform functions by operating on input data and generating output. Embodiments can be implemented advantageously in one or more computer programs that are executable on a programmable computer system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random-access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits), FPGAs and other forms of hardware.

What is claimed is:

1. A method implemented on a computer system, the computer system executing instructions to execute the method for generating a multi-ellipsoid head model used in dipole localization for a set of magnetic field sensors (MEG sensors), the method comprising:
    accessing locations of each MEG sensor from the set of MEG sensors; and
    for each MEG sensor from the set of MEG sensors, computing a corresponding ellipsoid subject to a plurality of constraints that prevent generation of a ghost ellipsoid, the computed ellipsoids used to model dipole localization in a brain's volume;
    wherein the plurality of constraints comprise:
        a first constraint that prevents generation of computed ellipsoids that completely encloses the brain's volume but have a center outside the brain's volume;
        a second constraint that prevents generation of computed ellipsoids that lie entirely outside the brain's volume; and
        a third constraint that requires that the center of the computed ellipsoid lies inside the brain's volume.

2. The computer-implemented method of claim 1 wherein the plurality of constraints further comprise a fourth constraint that prevents generation of computed ellipsoids that have a volume that is at least fifty percent non-overlapping with the brain's volume.

3. The computer-implemented method of claim 1 wherein at least one of the computed ellipsoids is a global sphere that is fit to an entire surface of the brain.

4. The computer-implemented method of claim 1 wherein the plurality of constraints further comprise a fourth constraint that a major axes of computed ellipsoids do not exceed a diameter of a smallest sphere that completely encloses the brain's volume.

5. The computer-implemented method of claim 1 wherein computing the corresponding ellipsoid comprises fitting an ellipsoid to a set of points on the brain surface relevant to the corresponding MEG sensor, and the plurality of constraints further comprise a fourth constraint that at least a predefined number of points are used to fit the ellipsoid.

6. A method implemented on a computer system, the computer system executing instructions to execute the method for generating a multi-ellipsoid head model used in dipole localization for a set of magnetic field sensors (MEG sensors), the method comprising:
    accessing locations of each MEG sensor from the set of MEG sensors; and
    for each MEG sensor from the set of MEG sensors, computing a corresponding ellipsoid subject to a plurality of constraints that prevent generation of a ghost ellipsoid, the computed ellipsoids used to model dipole localization in a brain's volume;
    wherein the plurality of constraints comprise:
        either a first set of constraints comprising (1) a center of the computed ellipsoid lies on a line through (a) a location of the corresponding MEG sensor, and (b) a point on the brain's surface closest to the corresponding MEG sensor; and (2) a major axis of the computed ellipsoid is not larger than a diameter of a smallest sphere that completely encloses the brain volume; OR a second set of constraints comprising (1) the center of the computed ellipsoid lies on a line through (a) the location of the corresponding MEG sensor, and (b) a center of a global sphere that is fit to the entire surface of the brain; and
        a third constraint that the computed ellipsoid includes the point on the brain's surface closest to the corresponding MEG sensor.

7. The computer-implemented method of claim 6 wherein the plurality of constraints include the first set of constraints.

8. The computer-implemented method of claim 6 wherein the plurality of constraints include the second set of constraints.

9. A method implemented on a computer system, the computer system executing instructions to execute the method for generating a multi-ellipsoid head model used in dipole localization for a set of magnetic field sensors (MEG sensors), the method comprising:
    accessing locations of each MEG sensor from the set of MEG sensors; and
    for each MEG sensor from the set of MEG sensors, computing a corresponding ellipsoid subject to plurality of constraints that prevent generation of a ghost ellipsoid, the computed ellipsoids used to model dipole localization in a brain's volume;
    wherein the plurality of constraints comprise a first constraint that the computed ellipsoid must have a center that lies along a line that traverses through at least two of the following three regions: (i) a location of the corresponding MEG sensor, (ii) a region of the brain's surface closest to the corresponding MEG sensor, and (iii) a location of the brain's volume.

10. The computer-implemented method of claim 9 wherein the line traverses through the location of the corresponding MEG sensor.

11. The computer-implemented method of claim 9 wherein the line traverses through the region of the brain's surface closest to the corresponding MEG sensor.

12. The computer-implemented method of claim 9 wherein the line is normal to the brain's surface.

13. The computer-implemented method of claim 9 wherein the plurality of constraints further comprise a second constraint that the center of the computed ellipsoid must lie within an area or volume defined by at least two of the following three regions: (i) the location of the corresponding MEG sensor, (ii) the region of the brain's surface closest to the corresponding MEG sensor, and (iii) the location of the brain's volume.

14. The computer-implemented method of claim 9 wherein the plurality of constraints further comprise a second constraint that the computed ellipsoid must have a major axis that does not exceed a maximum that is one of:

(i) a diameter of a largest sphere in a family of spheres that meet the first constraint and that is enclosed by the brain's volume, (ii) a diameter of a smallest sphere in the family that completely encloses the brain's volume, and (iii) a diameter of a smallest sphere in the family that has center inside the brain's volume.

15. The computer-implemented method of claim 9 wherein the plurality of constraints further comprise a second constraint that the computed ellipsoid includes a closest point on the brain surface to the corresponding MEG sensor.

\* \* \* \* \*